US008753582B2

(12) United States Patent
Gumbrecht et al.

(10) Patent No.: US 8,753,582 B2
(45) Date of Patent: Jun. 17, 2014

(54) APPARATUS AND METHOD COMPRISING A SENSOR ARRAY AND A POROUS PLUNGER AND USE THEREOF

(75) Inventors: Walter Gumbrecht, Herzogenaurach (DE); Peter Paulicka, Erlangen (DE); Manfred Stanzel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 710 days.

(21) Appl. No.: 12/867,561

(22) PCT Filed: Feb. 9, 2009

(86) PCT No.: PCT/EP2009/051428
§ 371 (c)(1),
(2), (4) Date: Aug. 13, 2010

(87) PCT Pub. No.: WO2009/101041
PCT Pub. Date: Aug. 20, 2009

(65) Prior Publication Data
US 2011/0021363 A1   Jan. 27, 2011

(30) Foreign Application Priority Data

Feb. 15, 2008 (DE) .......................... 10 2008 009 184

(51) Int. Cl.
| G01N 35/00 | (2006.01) |
|---|---|
| G01N 31/22 | (2006.01) |
| G01N 33/52 | (2006.01) |
| B01L 3/00 | (2006.01) |
| G01N 31/16 | (2006.01) |
| B01L 99/00 | (2010.01) |
| G01N 30/62 | (2006.01) |
| G01N 30/95 | (2006.01) |
| G01N 33/00 | (2006.01) |
| C12M 1/34 | (2006.01) |
| C12M 3/00 | (2006.01) |

(52) U.S. Cl.
USPC ........... 422/407; 422/552; 422/553; 422/569; 73/61.61; 435/7.92; 435/287.2

(58) Field of Classification Search
USPC .............................. 422/407, 569, 570; 506/7
See application file for complete search history.

(56) References Cited

U.S. PATENT DOCUMENTS 5,604,130 A * 2/1997 Warner et al. .............. 435/286.7
5,670,031 A * 9/1997 Hintsche et al. .......... 205/777.5
(Continued)

FOREIGN PATENT DOCUMENTS

DE  42 36 421 A1  5/1994
DE  43 18 519 A1  12/1994
(Continued)

OTHER PUBLICATIONS

Int'l. Search Report.

*Primary Examiner* — Jill Warden
*Assistant Examiner* — Julie Tavares
(74) *Attorney, Agent, or Firm* — Harness, Dickey & Pierce, P.L.C.

(57) ABSTRACT

Disclosed is an apparatus that is used for detecting liquids or substances from liquids and includes a plunger that has a porous plunger layer which is pressed onto a sensor array. Each sensor of the sensor array is surrounded by elevations which spatially separate the sensors from each other like walls. In at least one embodiment, when the plunger layer is pressed onto the sensor array, the walls are pressed into the pores of the plunger layer. Liquid-tight connections are created between the walls and the plunger layer while liquid remains over the sensors. The liquid can be measured. In at least one embodiment, when there is direct mechanical contact between the plunger layer and the sensors, the liquid over the sensors is located in open pores on the surface of the plunger layer. No liquid flows between the pores and across the walls when pressure is applied to the plunger layer such that closed reaction chambers are created.

19 Claims, 2 Drawing Sheets

(56) References Cited

U.S. PATENT DOCUMENTS

| | | |
|---|---|---|
| 6,037,168 A | 3/2000 | Brown |
| 6,921,514 B1 | 7/2005 | Vetter et al. |
| 2002/0164820 A1 | 11/2002 | Brown |
| 2003/0180190 A1 | 9/2003 | Corcoran et al. |
| 2004/0028875 A1 | 2/2004 | Van Rijn et al. |
| 2004/0029203 A1* | 2/2004 | Gumbrecht et al. ......... 435/7.92 |
| 2006/0088857 A1* | 4/2006 | Attiya et al. ...................... 435/6 |
| 2006/0108218 A1* | 5/2006 | Gephart et al. ............... 204/400 |
| 2009/0305397 A1 | 12/2009 | Dodgson et al. |

FOREIGN PATENT DOCUMENTS

| | | |
|---|---|---|
| DE | 100 58 394 C1 | 7/2002 |
| WO | WO 01/54814 A2 | 8/2001 |
| WO | WO 02/43937 A2 | 6/2002 |
| WO | WO 2006/097751 A2 | 9/2006 |

\* cited by examiner

APPARATUS AND METHOD COMPRISING A SENSOR ARRAY AND A POROUS PLUNGER AND USE THEREOF

PRIORITY STATEMENT

This application is the national phase under 35 U.S.C. §371 of PCT International Application No. PCT/EP2009/051428 which has an International filing date of Feb. 9, 2009, which designates the United States of America, and which claims priority on German patent application number DE 10 2008 009 184.7 filed Feb. 15, 2008, the entire contents of each of which are hereby incorporated wherein by reference.

FIELD

At least one embodiment of the present invention generally relates to an apparatus comprising a sensor array and comprising a plunger, and/or to a method using the apparatus for detecting liquids or substances from liquids in spatially different reaction regions. At least one embodiment of the invention furthermore relates to the use thereof in a smart card.

BACKGROUND

In sensor technology, sensor arrays are increasingly being used in order to be able to detect a plurality of chemical compounds simultaneously. These sensor arrays are used especially in bioanalysis technology, e.g. for DNA analysis, for detecting pathogens or for examining metabolic disturbances. In this case, body fluids such as e.g. blood or urine are worked up by way of chemical reactions. They are then conducted via the sensor arrays and interactions between the sensors of the sensor arrays and the substances to be detected from the body fluids are examined by means of optical, frequency or electrochemical measurements. In this case, the sensors of the sensor arrays are often coated with molecules which react specifically with the substances to be detected from the body fluids. By means of washing with liquids, unbound substances can be removed from the surfaces of the sensors. The specifically bound substances to be detected can then be detected directly or indirectly, e.g. by means of markers.

Typical detection methods comprise optical measurements, frequency measurements or electrochemical measurements. Thus, by way of ellipsometry, for example, it is possible to examine the changes in the refraction properties of the surface after the binding of the substances to be detected. An alternative is the binding of specific, optically active markers to the substances to be detected. These can be detected e.g. by way of their fluorescence or visible color upon irradiation with specific wavelengths. Frequency measurements using a quartz microbalance can detect changes in the mass of molecules bound to the surface. Current-voltage measurements with the aid of electrodes in a liquid can electrochemically detect the binding of the substances to be detected, or the bound state thereof directly or by way of reaction products.

What the methods described have in common is that indefinite flow conditions above the sensors can lead to measurement errors. Depending on the flows, different double layers form at the boundary layers between the sensor surfaces and the liquid or molecules bind non-specifically to the surfaces, as a result of which e.g. the reactivity, the binding affinity and the optical, electrical and friction properties of the sensor surfaces change.

The production of constant flows above the sensors of the sensor arrays is complex and requires a high outlay in respect of apparatus. Therefore, measurement is preferably carried out with stationary liquids, that is to say without disturbing flows above the sensors.

The document DE 100 58 394 C1 describes an arrangement and a method for producing stationary liquids above sensors of sensor arrays. The sensors of a sensor array are arranged on a planar surface with walls between the individual sensors, wherein the walls project from the surface. A housing upper part is arranged parallel to the planar surface of the sensor array at a distance from the walls, said housing upper part being at a sufficient distance from the surface and the walls to allow liquid to flow between the surface and the housing upper part. Before the measurement, the housing upper part is pressed in the direction of the surface with walls with the aid of a plunger, such that the walls and the housing upper part are in close contact.

The flowing of the liquid has been prevented, and closed-off reaction spaces, delimited by the planar surface, the walls and the housing upper part, have been produced above the sensors. The liquid which has been enclosed in the reaction spaces can then be examined without exchange of liquid between different reaction spaces. The measurement of the sensors takes place with the aid of the closed-off reaction spaces independently of one another.

The method described in accordance with DE 100 58 394 C1 leads to an arrangement with housing upper part and plunger in which the walls between the sensors have to correspond to precise dimensions. These precise dimensions are difficult to realize in practice:

If the walls project too little from the planar surface in which the sensors are arranged, then this gives rise to reaction spaces which are too small and have an amount of liquid that is too small to carry out a meaningful measurement. The housing upper part can, under certain circumstances, be seated on the sensors at high plunger pressure, whereby the measurement is corrupted.

If the dimensions of the walls are made too large, then the sensors have to be arranged at a larger distance from one another, and the required amount of liquid for filling the arrangement increases. This means that the sensitivity of the measurement turns out to be lower and the number of sensors available for measurement decreases for the same area since the dimensions of said sensors have to be made larger in order to achieve a sufficient measurement accuracy.

SUMMARY

At least one embodiment of the invention specifies a relatively simpler, less error-prone and more cost-effective apparatus and method and the application thereof for detecting liquids or substances in liquids. In particular, at least one embodiment of the invention reduces the dependence of the measurement accuracy and the reliability of the apparatus on the fault tolerances of the production of the walls between the sensors. A simpler construction with fewer fault possibilities is intended to save costs in the production of the apparatus and to increase the measurement accuracy. The possibilities of damage to the apparatus in use are intended to be reduced.

Advantageous configurations of the apparatus according to embodiments of the invention, of the method and of the use thereof emerge from the respectively assigned dependent claims. In this case, the features of the alternative independent claims can be combined with features of a respectively assigned dependent claim or preferably also with features of a plurality of assigned dependent claims.

The apparatus according to at least one embodiment of the invention for detecting liquids or substances from liquids in reaction spaces that are spatially separated from one another comprises a sensor array and a plunger. The sensor array is composed of at least two sensors. The plunger has a plunger layer at its surface lying opposite the sensor array and is arranged such that it is movable relative to the sensor array. The plunger layer can be brought into mechanical contact with the sensor array. It has at least partly or completely porous properties and is impermeable to liquids or substances from liquids relative to the total layer thickness of the plunger layer.

In one example embodiment of the apparatus according to the invention, the at least two sensors are arranged on or in or below a first surface, in particular a first planar surface, and a second surface, in particular a second planar surface, is formed by the surface of the plunger layer which lies opposite the sensor array.

In a further example embodiment, the plunger can be arranged in a first position such that the second surface is at a distance from the first surface, in particular a distance in the range of micrometers or millimeters, and the plunger can be arranged in a second position such that the second surface and the first surface are in direct contact.

Preferably, the pores of the porous plunger layer have a diameter in the range of 0.05 to 100 micrometers, particularly preferably in the range of 1 to 10 micrometers.

Furthermore preferably, between the at least two sensors, elevations project from the first surface, which in each case completely surround or enclose the sensors particularly in the plane of the first surface and whose height with which the elevations project from the first surface is greater than any height of structures which are arranged within parts of the first surface which are surrounded or enclosed by the elevations.

The height and/or width of the elevations between the at least two sensors are/is preferably of the order of magnitude of the diameters of the pores of the plunger layer, in particular in the range of 0.05 to 100 micrometers, particularly preferably in the range of 1 to 10 micrometers. Particularly preferably, in the second position of the plunger, the elevations projecting from the first surface can be arranged partly or completely in the pores of the plunger layer.

In one example embodiment of the apparatus, as a result of a direct contact between the elevations and the plunger layer, a gas- or liquid-tight connection exists and/or gas or liquid exchange is only possible via those pores which are arranged directly above the sensors.

In a further example embodiment of the apparatus, the space between the sensor array and the plunger layer can be filled or is filled partly or completely with liquid and/or only pores, at the surface of the porous plunger layer can be filled or are filled with liquid, wherein pores inside the plunger layer do not contain any liquid and/or cannot be filled with liquid.

In a particular example embodiment of the apparatus according to the invention, the at least two sensors are electrochemical sensors, in particular metal electrodes arranged in finger-shaped fashion on the first surface. They can be constructed from gold, silver and/or silver chloride, platinum, palladium and/or copper or contain compounds or alloys of said metals.

In a further example embodiment of the apparatus, the porous plunger layer is formed from a porous material which contains porous plastic, porous rubber or porous natural rubber or is formed therefrom. In particular, the porous plunger layer is composed of a material which is elastically deformable, or is composed of a plastically deformable material, in particular porous silicon, porous glass or porous plastic, and the elevations are constructed from an elastic material.

The layer thickness of the plunger layer is preferably in the range of micrometers, or in the range of millimeters, or in the range of centimeters, and/or the plunger is completely composed of the plunger layer.

The method according to at least one embodiment of the invention for detecting liquids or substances from liquids in reaction spaces that are spatially separated from one another comprises the temporally successive steps of:

filling a space with a liquid and/or causing a liquid to flow through a space, which space is formed by the interspace between a surface of a sensor array, comprising at least two sensors, and a surface of a plunger layer, which has at least partly or completely porous properties and is impermeable to liquids or substances from liquids relative to the total layer thickness of the plunger layer, moving or pressing the plunger layer in the direction of the sensor array with the aid of a plunger connected to the plunger layer until the surface of the sensor array is in direct mechanical contact with the surface of the plunger layer, measurement by means of the sensors of the sensor array.

Preferably, the method is carried out in the form that, during the direct contact between the surface of the sensor array and the surface of the plunger layer, no liquid exchange takes place, in particular between each liquid-filled region directly above a first sensor of the at least two sensors of the sensor array and each liquid-filled region directly above the at least one second sensor.

Particularly preferably, the liquid-filled regions above the sensors are formed exclusively by regions which are composed of liquid-filled pores at the surface of the porous plunger layer. The pores which are not connected to the surface of the plunger layer and are arranged inside the porous plunger layer are not filled with liquid.

In a further example embodiment of the method according to the invention, closed-off reaction spaces are formed, in particular liquid-filled reaction spaces, while the surface of the sensor array is in direct mechanical contact with the surface of the plunger layer. The closed-off reaction spaces are formed, in particular, by elevations on the surface of the sensor array between the sensors, by the surface of the sensor array and by the pores of the porous plunger layer which are open toward the surface of the plunger layer.

In a particular example embodiment of the method according to the invention, the sensors carry out electrochemical measurements, in particular voltametric and/or chronoamperometric and/or coulometric and/or impedance measurements. The measurements of the sensors can be effected simultaneously or successively.

In a further embodiment of the method, the surface of the plunger layer which lies opposite the sensor array and the surface of the sensor array are moved toward one another parallel to one another. In this case, they are oriented parallel to one another in particular before, after and at every instant of the movement. The plunger layer is preferably moved in a direction perpendicular to the surface of the sensor array. In this case, the plunger layer can be moved in the direction of the sensor array, or the sensor array can be moved in the direction of the plunger layer, or the sensor array and the plunger layer can both be moved toward one another simultaneously.

The use of the above-described apparatus and/or of the method comprises the use in a smart card or cassette, in particular in a disposable smart card or disposable cassette, comprising a chip, e.g. a CMOS chip comprising a sensor array, in particular comprising electrochemical sensors, wherein the chip is cast in particular in a polymeric potting compound, such as e.g. plastic. The plunger layer is e.g. applied or introduced into cutouts or onto the surface of the disposable smart card or disposable cassette by means of an injection-molding method.

In this case, the smart card can be inserted into a read-out device, in particular into a handheld read-out device, which contains, in particular, a voltage and/or current source, a display, a digital interface for the chip, a signal processing unit, an electrical, particularly preferably a thermostatically regulated electrical, tap, a plunger actuator and/or reagent actuator.

If a pressure is exerted by the read-out device on the smart card, in particular areally via the plunger, then the plunger layer pressed onto the chip is brought into mechanical contact with the chip surface in such a way that regions filled with liquid to be analyzed, in particular pores, at the surface of the plunger layer do not exchange liquid across different sensors. Closed-off reaction regions are thus formed above the respective sensors.

The use of the above-described apparatus and/or of the method includes a use in an immunological fast test and/or in a blood test and/or in a DNA or RNA analysis and/or in an antibody test and/or in a peptide test.

At least one embodiment of the invention is based generally on the concept that, in the case of measurements in liquids with a plurality of sensors of a sensor array, reaction spaces that are separated from one another are created above the sensors. The reaction spaces arise with the aid of a plunger having at its surface a porous plunger layer that is impermeable to liquids relative to its total thickness. In particular, on the surface of the sensor array between the sensors there are respective elevations or walls which completely separate or demarcate the sensors from one another, as viewed in the plane of the surface. The plunger can be pressed in the direction of the surface of the sensor array, wherein the walls press into the plunger layer or are pressed into the pores of the plunger layer. A possible liquid flow or liquid exchange by way of the walls is thereby prevented. Through open pores at the surface of the plunger layer which are filled with liquid, a liquid exchange can take place directly above the sensors. The plunger layer can be pressed onto the surface of the sensor array and be seated on said surface without completely displacing the liquid above the sensors. With the use of a plunger layer composed of elastic material or walls composed of elastic material, it is possible to prevent irreversible deformations or damage of the elevations or walls when the plunger layer is pressed onto the sensor array.

Measurements with reduced measurement errors are thus possible, with no disturbing liquid flows across the entire sensor array or simultaneously across adjacent sensors. The technical outlay for the production of the apparatus is reduced relative to apparatuses known from the prior art with rigid plungers and smooth plunger surfaces. Greater manufacturing tolerances are possible during the production of the elevations or walls which demarcate or separate the sensors from one another in the plane of the surface of the sensor array. The apparatus and the measuring method are less dependent on the dimensioning of the plunger pressure with which the plunger is pressed onto the surface of the sensor array.

The abovementioned advantages associated with the apparatus according to at least one embodiment of the invention emerge for the method according to at least one embodiment of the invention and the uses according to at least one embodiment of the invention.

BRIEF DESCRIPTION OF THE DRAWINGS

Example embodiments of the invention with advantageous developments in accordance with the features of the dependent claims are explained in greater detail below with reference to the following figures, but without being restricted thereto.

In the figures.

DETAILED DESCRIPTION OF THE EXAMPLE EMBODIMENTS

Figure 1:
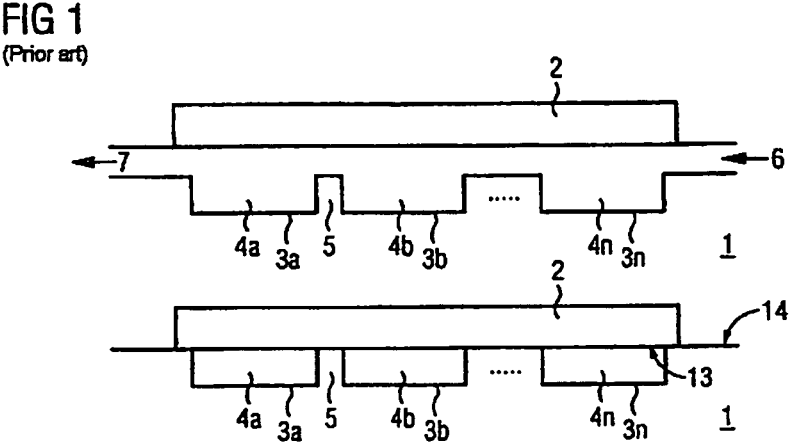
FIG. 1 shows a schematic illustration of a known sensor array 1 before A) and during B) the measurement, with reaction spaces 4 assigned to sensors 3 and with a stiff, compact plunger 2 having a smooth, closed surface, for sealing the reaction spaces 4 from liquid exchange.

FIG. 1 illustrates a known apparatus, such as is known e.g. from the document DE 10058394 C1, in the open state (subfigure A)) and in the closed state (subfigure B)). The apparatus comprises a sensor array 1, which is constructed from sensors 3a to 3n that are spatially at a distance from one another. The sensors 3a to 3n are arranged in the form of an array on a planar surface. Between the sensors 3, walls 5 project from the planar surface. The walls 5 surround the sensors 3 completely, e.g. in the form of closed rings around each individual sensor 3a to 3n.

A stiff plunger 2 is arranged at a small distance, e.g. in the range of micrometers to centimeters, parallel to the planar surface. Stiff plunger 2 in this context means a plunger composed of a material that is incompressible or compressible only to a very small extent. Liquid can flow in the interspace between the stiff plunger 2 and the planar surface of the sensor array 1 with walls 5. For this purpose, microchannels can be formed in the planar surface adjacent to the sensor array 1, said microchannels serving as inlet 6 and outlet 7. If the plunger 2 is pressed in the direction of the planar surface of the sensor array 1, then it comes into direct mechanical contact with the walls 5.

If the walls 5 are embodied such that they project from the planar surface with identical heights and completely enclose or encompass each sensor 3, then the plunger 2, given parallel orientation of its planar plunger surface with respect to the planar surface of the sensor array 1, is in contact with all walls 5 simultaneously and the liquid flow is completely prevented. Reaction spaces 4a to 4n are formed, which are filled with liquid, and which are delimited by the planar surface in which the sensors 3a to 3n are arranged, the walls 5 and the plunger 2. No liquid exchange takes place between different reaction spaces 4a to 4n. In the case of a measurement by means of the sensors 3a to 3n successively or simultaneously, different reactions in different reaction spaces 4a to 4n cannot mutually influence one another. The prevented liquid exchange between reaction spaces 4a to 4n can likewise lead to a measurement with a smaller measurement error in comparison with measurements in the case of open reaction spaces 4a to 4n, cf. FIG. 1A).

One example of measurements by way of sensors 3 in which closed-off reaction spaces 4a to 4n lead to a reduction of measurement errors is electrochemical measurements. The sensors 3 in the case of electrochemical measurements are composed, for example, of metal electrodes 8, e.g. gold electrodes applied in a finger-shaped fashion on the planar surface.

The electrodes can be coated with catcher molecules, in a manner specific to the molecules to be detected in the liquid. By way of example, a fixed voltage is applied to the sensors 3, that is to say gold electrodes, and a current flow to be measured changes depending on molecules binding to the surface. Further known electrochemical methods are cyclic voltametry, chronoamperometry, coulometry, impedance spectroscopy, which differ in the measurement variables to be controlled by open-loop or closed-loop control and/or in the open-loop or closed-loop control methods for current and voltage.

What is common to the methods is that the measurement results depend greatly on whether the liquid to be measured is present in a stationary fashion or as a flow above the sensors 3. A subtle measurement with no disturbing measurement signals is possible only in the case of a stationary liquid or liquid that flows in a constant fashion. The simplest measurement set-up that can be realized technically consists in the realization of a stationary liquid, such as is present e.g. in the apparatus shown in FIG. 1B).

However, in order to realize a stationary liquid without flows during a measurement, the reaction spaces 4a to 4n have to be completely separated from one another. This is only the case if the plunger 2 is in close contact simultaneously with all walls 5 and there is no distance between any wall and the plunger 2. This is only possible if all walls 5 project from the planar surface of the sensor array 1 with the same height. Such an apparatus presupposes very complex production methods and precise inspection of the dimensions after the production of the apparatuses.

Figure 2:
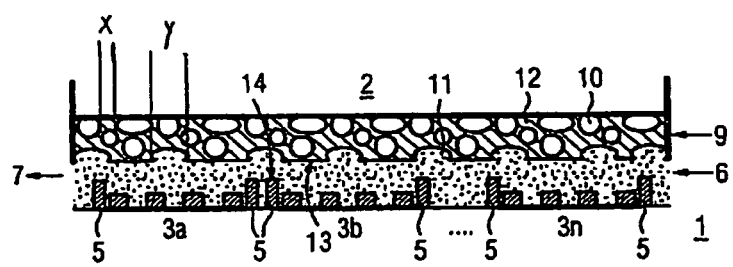
FIG. 2 shows a schematic illustration of a sensor array 1 having sensors 3, which are spatially separated from one another by walls 5, and a plunger 2 having a porous plunger layer 9, the pores of which at the surface are filled with liquid and the pores of which in the inner region do not contain liquid, before C) and during D) the pressing of the plunger layer 9 onto the surface of the sensor array 1 or before C) and during D) the measurement
Figure 2:
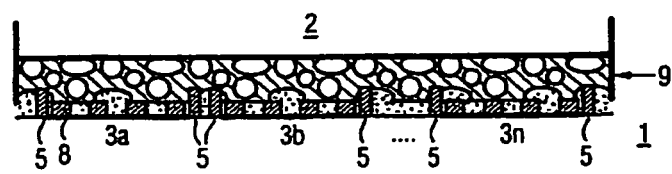

FIG. 2 illustrates an apparatus in accordance with one example embodiment of the invention. A sensor array 1, constructed analogously to the above-described sensor array 1 from the prior art, composed of sensors 3a to 3n that are spatially separated from one another, is arranged in a planar surface on a substrate. The sensors 3 are composed, for example, of gold electrodes arranged in a finger-shaped fashion. FIG. 2 illustrates a section through the apparatus, and thus through the finger-shaped electrodes 8. Further electrode materials which can be used are metals such as e.g. silver or silver chloride paste, palladium, copper, platinum or platinized platinum, semiconductor materials such as e.g. titanium oxide or silicon, materials such as e.g. graphite, glass carbon and compounds of the materials mentioned.

Walls 5 are arranged between the electrodes 8, said walls separating the electrodes 8 spatially from one another, at least in the planar plane. The walls 5 can be embodied in the form of closed rings lying flat on the planar surface, or in the form of rectangular boundaries (analogously to the boundaries of the squares on a chessboard), or in the form of triangular boundaries, or in the form of a honeycomb structure. Structures which span the area as completely as possible like a network are preferred.

The walls 5 are preferably formed from the same material as the carrier substrate on which the electrodes 8 are arranged. Possible materials are silicon, silicon oxide, plastic such as e.g. polyimide, glass or photoresist such as e.g. PBO (polybenzoxazole). However, the invention is not restricted to these materials. The walls 5 can also be composed of different materials than the carrier material.

In particular, the walls 5 can be composed of elastic or readily plastically deformable materials such as e.g. plastics, rubber or natural rubber or readily deformable resists and sealing materials such as e.g. Teflon or PCTFE (polychlorotrifluoroethylene). In the case of materials of the plunger layer 9 that are plastically deformable with difficulty, such as e.g. porous silicon oxide or porous glass, the readily deformable walls result in the apparatus having good sealing properties when the walls 5 are brought into contact with the porous plunger layer 9.

The walls 5 can be etched or stamped from the surface, vapor-deposited or sputtered, or applied in the form of photoresist. However, the invention is not restricted to walls 5 produced according to the methods mentioned above. A large number of further methods are conceivable. One further method is to arrange the sensors 3 in depressions in the surface, in an area parallel to the planar surface. The walls 5 and the carrier material are preferably not permeable to liquid.

As is illustrated in FIG. 2, a porous plunger layer 9 is arranged opposite the planar surface of the sensor array 1 with walls 5 between the sensors 3. In the initial state, the porous plunger layer 9 is arranged at a distance from the planar surface of the sensor array 1 and at a distance from the walls of the planar surface, see figure part C). The distance can be in the range of micrometers, or in the range of millimeters, or in the range of centimeters. Preferably, the porous surface of the plunger layer 9, without considering the open pores 11, is arranged in a planar fashion and parallel to the planar surface of the sensor array 1.

The interspace between the planar surface of the sensor array 1 and the porous surface of the plunger layer 9 can be filled with liquid. The liquid can be supplied in an inlet 6, flow through the interspace and be discharged or removed in an outlet 7.

Examples of liquids which can be examined by way of the apparatus illustrated are body fluids such as blood or urine or saliva, whose constituents or reaction products after e.g. disintegration reactions are detected. By way of example, DNA molecules or fragments can thus be detected or analyzed with the aid of the sensors 3, and viruses or antibodies, peptides or other biochemical compounds such as e.g. enzyme substrate solutions can be examined.

As liquids, however, it is also possible to examine waste water with chemical contaminants or drinking water or detect other chemical substances in liquids.

Before, after and in intermediate steps of the examination of the liquids, the interspace and the surfaces of the plunger layer 9 and also of the sensor array can be cleaned using purging liquid, e.g. tridistilled water or alcohol or other solvents. The purging liquid is flushed through the interspace once or repeatedly. Cleaning by purging using air or other gases is also possible. Especially in order to remove residues of the purging liquid, the interspace, the plunger layer 9 with the open pores 11 and the surface of the sensor array 1 with the sensors 3 and walls 5 can be dried and cleaned after a purging process using nitrogen, for example.

When liquid is filled into and flows through the interspace between sensor array 1 and plunger layer 9, preferably the entire space of the interspace is filled with liquid. Air bubbles or gas bubbles can be avoided by shaking and special filling steps. Hydrophilic coatings can also lead to better wetting and to avoidance of air bubbles during filling. The plunger layer 9 should not be filled with liquid in its inner region. The material of the plunger layer 12 is liquid-impermeable, at least to the liquid to be examined. Only the pores 11 of the plunger layer 9 that are open toward the surface are filled with liquid.

On the opposite side to the plunger layer 9, the sensors 3 and the walls 5 are in contact with the liquid. Preferably, the entire surface of the sensor array 1 or of the sensors 3 with the walls 5 situated on the surface is completely wetted. Air bubbles adhering to the surface can disturb or prevent measurements.

The plunger layer 9 can be applied fixedly or loosely on a compact plunger 2 or first come into contact with the latter when the plunger layer 9 is pressed in the direction of the sensor array 1. Fixed application can be effected in the form of adhesive bonding or soldering and other connecting methods. However, the plunger can also be completely composed of the plunger layer 9, or the plunger layer 9 can be produced e.g. by etching at the surface of the plunger. A porous construction of the plunger layer with open pores 11 at the surface of the plunger layer 9 is essential. The plunger layer 9 can also be fitted in the form of a film opposite the sensor array, with open pores 11 at the surface and closed pores 10 inside the plunger layer 9. The closed pores 10 of the plunger layer 9 can be filled with air or a gas.

Before a measurement by way of the sensors 3 of the sensor array 1, the plunger layer 9 is displaced in the direction of the surface of the sensor array 1. This is preferably effected by means of a pressure on the rear side of the plunger layer 9. The rear side is that side of the plunger layer 9 which lies opposite the porous surface of the plunger layer 9, which is arranged opposite the surface of the sensor array 1. The rear side is in contact or is brought into contact with the plunger 2. Preferably, the plunger 2 exerts a uniform pressure areally on the entire rear side of the plunger layer 9.

As a result, the plunger layer 9 is moved in the direction of the surface of the sensor array 1. The movement is preferably effected in a form in which the porous surface 13 of the plunger layer 9 is moved toward the surface of the sensor array 1 parallel to the planar surface of the sensor array 1. The movement can be effected uniformly at a fixed speed or in an accelerated fashion.

As a result of the movement of the plunger layer 9 in the direction of the sensor array 1, part of the liquid is displaced from the interspace. The liquid can flow away via the outlet 7. Instead of the plunger layer 9, the sensor array 1 can also be moved in the direction of the plunger layer 9, or the plunger layer 9 and the sensor array 1 can be moved simultaneously toward one another.

The movement is effected until there is a sufficient contact between the plunger layer 9 and the sensor array 1 with sensors 3 and walls 5. If the pressure exerted by the plunger 2 on the rear side of the plunger layer 9 is equal to the counterpressure on the plunger layer 9 from the sensor array 1, then the movement of the sensor array 1 and the plunger layer 9 toward one another is completed.

After completion of the movement, walls 5 have been pressed into the open pores 11 of the plunger layer 9 and result in a tight connection of the walls 5 to the plunger layer 9 across which a liquid transfer can no longer take place or is at least greatly restricted. Liquid-tight connections arise between the walls 5 and the plunger layer 9, preferably in the case of deformable walls 5 and/or a deformable plunger layer. Given sufficient pressure, liquid-tight connections can also arise if the walls 5 and the plunger layer 9 are composed of materials that are of similar or identical strength or are similarly or identically non-deformable, or the walls 5 are composed of stronger material than the plunger layer 9. In this case, the walls 5 are pressed into the open pores 11 until they touch and cut the material of the plunger layer 9 in the pores 11 or are squeezed into the webs of the material of the plunger layer 9 which demarcate individual open pores 11 from one another.

After completion of the movement, liquid to be examined is also present above the sensors 3. The sensors 3 are in contact with the liquid and can measure and detect substances in the liquid or constituents of the liquid. Chemical reactions which take place in the liquid can be observed in a temporally resolved manner with the aid of the sensors 3.

In the case where the plunger layer 9 is in direct contact with the sensors 3 or with the electrodes 8 of the sensors, the liquid in the open pores 11 is in contact with the sensors 3. The material 12 of the plunger layer 9 is seated on the electrodes 8 or is in direct mechanical contact with the latter.

Even in the case where walls 5 are not present, this results in prevention or great reduction of liquid flow above the sensors 3. Consequently, an apparatus without walls 5 likewise results in a reduction of measurement errors or noise during the measurement.

In one example embodiment, the electrodes 8 of the sensors 3, particularly preferably the totality of the electrodes 8 of a respective sensor 3, are smaller than the diameter of the pores 11 of the plunger layer 9. Thus, the electrodes 8 can be e.g. finger-shaped with fingers having a width of 1 μm which are arranged at a distance from one another of 1 μm, and have a height of up to 0.5 μm. The sensor 3 is composed e.g. of two comb-shaped, mutually intermeshing electrode systems which form a sensor 3 having a width of approximately 150 μm to 200 μm. The sensor 3 is arranged centrally e.g. between walls having a width of 20 μm and a height of 5 μm, and produces in totality a circle having a diameter of 150 μm, wherein the walls circularly enclose an inner space with sensor 3 having a diameter of e.g. 200 μm. In this exemplary embodiment, a pore 11 would have a diameter of between 2 μm and 200 μm (Y in FIG. 2), particularly preferably a diameter which allows a pore 11 to extend over at least two adjacent electrodes, e.g. in the range of 2 μm to 5 μm (X in FIG. 2), with a depth into the plunger layer 9 of the order of magnitude of 5 μm to 200 μm. Consequently, a pore 11 can form a complete reaction space or reaction chamber 4 above a sensor 3 or a reaction space or reaction chamber 4 which extends over at least two adjacent electrodes. In the case of pressure on the plunger layer 9, the volume of the pores 11 can be decreased, and an increase in the concentration of reaction products can be achieved as a result of the reduction of the volume. The sensitivity of the apparatus is thus increased or the detection limit is improved, that is to say that the minimum concentration of the substances to be detected which can be detected by way of the apparatus is reduced.

One advantageous embodiment of the apparatus according to the invention with walls 5, such as is illustrated in FIG. 2, leads to the formation of closed-off reaction spaces 4. The closed-off reaction spaces 4 are formed after completion of the movement and are delimited by the plunger layer 9 with open pores 11, the sensor array 1 with electrodes 8 situated thereon, and the walls 5, which completely surround or enclose the sensors 3 in the plane of the surface of the sensor array 1.

The closed-off reaction spaces 4 lead, in addition to the prevention of flows of the liquid across a plurality of sensors 3, to the decoupling of reactions in reaction spaces 4 that are spatially separated from one another. Thus, in different reaction spaces 4, reactions can proceed independently of one another and be measured in a temporally resolved manner by means of the sensor 3 situated in the respective reaction space 4, or the reaction result can be measured, independently of the reaction result in an adjacent reaction space 4.

After completion of the movement of the plunger layer 9 and/or of the sensor array 1, the plunger layer 9 can be in direct contact with the electrodes 8 of the sensors, or be at a small distance therefrom. Thus, the plunger layer 9 can e.g. be in contact with the walls 5 and, in particular, form closed-off reaction spaces 4, and be at a distance from the sensors 3 or electrodes 8 of the sensors 3 which is preferably in the range of micrometers, or in the range of millimeters, or in the range of centimeters, depending on the dimensions of the walls 5.

Figure 3:
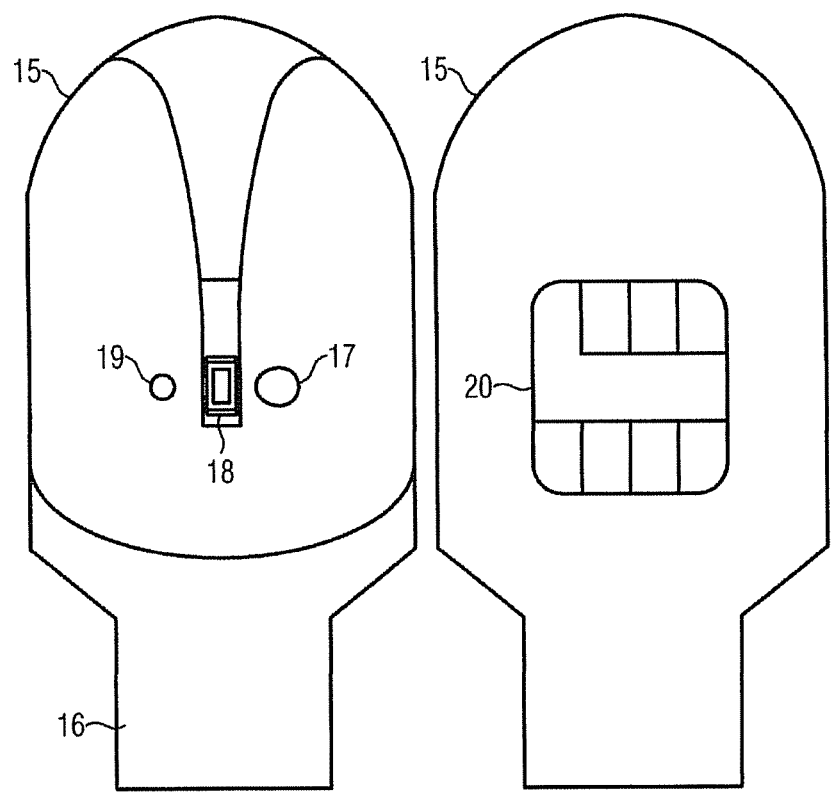
FIG. 3 shows a schematic illustration of the front side E) and rear side F) of a plug-in module for immunological fast tests.
Figure 4:
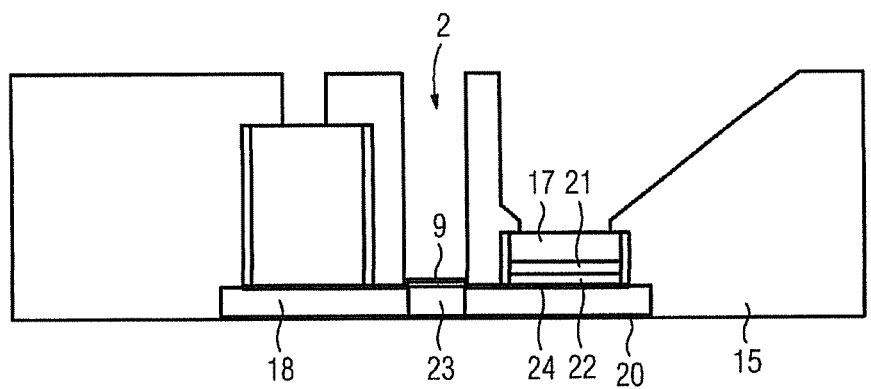
FIG. 4 shows a schematic illustration of a cross section through the plug-in module shown in FIG. 3.

FIGS. 3 and 4 illustrate a plug-in module for immunological fast tests as one possible application of the apparatus according to at least one embodiment of the invention and of the method according to at least one embodiment of the invention.

In this case, FIG. 3 shows the front side E) and rear side F) of the plug-in module, which is composed e.g. of a plastic body as housing 15 and, situated therein, a chip module 18 with a sensor array 1 on a chip 23, electrical contacts 20, and microchannels 24 on the chip module 18. The plug-in module can have the form illustrated in FIG. 3 or other forms, such as e.g. that of a check card. Chambers and microchannels for the take-up, transport and reactions and also release of the liquid are formed in the plastic housing 15. Chambers for reagents, such as dry reagents, for example, which are required for disintegration and detection reactions, for example, can likewise be realized in the plastic housing 15.

For better handling, the housing 15 can be equipped with a handle 16 and with inscriptions, such as e.g. patient or sample data. As an alternative, data can be stored on the chip 23, which is e.g. a CMOS chip (Complementary Metal Oxide Semiconductor), with a sensor array 1 situated thereon and a data processing and/or memory device integrated in the chip 23.

Liquid is supplied to the housing 15 via an inlet 17 in the housing 15. The liquid is conducted through the microchannels 24 over the chip 23 and the sensor array 1. Before the measurement begins, a plunger 2 with plunger layer 9 is pressed onto the chip 23 with sensor array 1. The plunger layer 9 may previously be situated at a distance from the sensor array 1 on the chip 23 in order to cover the sensor array 1 and to protect it from contaminants. Alternatively, the plunger layer 9 is fixedly connected to the plunger 2 and is therefore first pressed onto the chip 23 with the action of the plunger on the sensor array 1. In this case, the sensor array 1 is open toward the top, that is to say not encapsulated by the housing 15 and closed off from the environment. The plunger 2 with plunger layer 9 is pressed onto the chip 23 with sensor array 1 until completion of the measurement. Excess liquid and also liquid after the measurement, when the pressure from the plunger 2 with the plunger layer 9 has been canceled, can be disposed of in an outlet 19 with venting or can be removed from the housing 15 via said outlet.

The plunger 2 is preferably integrated in a measuring apparatus (not illustrated) comprising the measuring electronics.

The sensor array 1 is contact-connected via the chip 23 and electrical contacts 20 which are electrically connected to the chip 23 and are situated on the rear side of the housing. When the plug-in module is inserted into the measuring apparatus, electrical contact between the measuring apparatus and the electrical contacts 20 of the plug-in module is established. The sensor array 1 can be electrically addressed via the measuring electronics of the measuring apparatus, and measurement variables can be communicated to the measuring electronics, which are then processed and evaluated in the measuring apparatus. A display or other optical and acoustic output devices, which are connected to the measuring apparatus, can output the measurement result.

FIG. 4 illustrates a section through the plug-in module shown in FIG. 3. An enzyme substrate pad 21, a conjugate pad 22, the chip module 18 with a sensor array 1 on e.g. a CMOS chip 23 and also microchannels 24 arranged thereon are integrated in the housing 15. The liquid to be examined, e.g. blood, can be supplied via a liquid inlet 17. The liquid flows through the enzyme substrate pad 21 and the conjugate pad 22, for example. Further substance pads can also be integrated, which mix the liquid to be examined with chemical substances and prepare it for the examination by means of chemical reactions. By way of example, blood can be used as the liquid. The blood is disintegrated, that is to say that the cells release constituents such as DNA, for example, which are in turn decomposed into small fragments. In one example embodiment, the fragments are subsequently bound to markers that enable the fragments to be detected.

The liquid prepared in this way is conducted to the sensor array 1 via the microchannels 24, that is to say that, by way of capillary forces and/or an external pressure or gravitational forces, the liquid is sucked up by the microchannels 24 and/or the microchannels 24 are filled with the liquid. The liquid is transported to the sensor array 1 via the microchannels 24 and conducted over the sensor array 1. An opening in the housing above the chip 23 enables pressure to be supplied in the direction of the chip 23. The pressure can be supplied in the form of air pressure or directly with the aid of a plunger 2. The plunger layer 9 may be fixed to the plunger or may previously have been placed on the chip 23. As an alternative, the plunger layer 9 may also already be integrated in the housing 15 at a distance, arranged above the chip 23. In this case, it protects the chip 23 or the sensor array 1 from contamination before, during and after use.

In the embodiment of the inventive apparatus as illustrated in FIG. 4, the plunger 2 presses directly onto the plunger layer 9 via the opening in the housing 15, said plunger layer moving in the direction of the sensor array 1 until the plunger layer 9 is in direct contact with the electrodes 8 of the sensors 3. Between the walls 5 and the plunger layer 9 there is a liquid-tight connection, whereby closed-off reaction spaces 4 filled with liquid have been formed. Measurements by way of different sensors 3a to 3n can be carried out independently of one another, simultaneously or successively. Liquid flows across a plurality of reaction spaces 4 are prevented and do not lead to interference signals during the measurement or to measurement errors.

Instead of pressure being exerted on the plunger layer 9 directly by the plunger 2, pressure can also be exerted on the plunger layer 9 indirectly by way of housing parts 15 if the plunger layer 9 is completely integrated in the housing and covered by the latter.

After the reactions and the measurements with the aid of the sensors 3 have proceeded, the pressure on the plunger layer 9 is canceled, and the liquid can flow into a liquid outlet 19.

It can remain there or be removed for further examinations. The liquid outlet 19 likewise serves for disposing of an excess amount of liquid before the measurements and for disposing of e.g. purging liquids that are used before and after measurements for purging the interspace between plunger layer 9 and sensor array 1.

The plug-in module can be designed for single use, that is to say as a disposable module, or for repeated use.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. An apparatus comprising:
a sensor array including at least two sensors separated by walls; and
a plunger for detecting liquids or substances from liquids in reaction spaces that are spatially separated from one another when the plunger is in contact with the sensor array, the plunger being arranged to be movable relative to the sensor array and including a plunger layer, at a surface lying opposite the sensor array, capable of being brought into mechanical contact with the sensor array, the plunger layer further including at least partly or completely porous properties and being impermeable to liquids or substances from liquids relative to a total layer thickness of the plunger layer, wherein the pores are configured to receive the walls in open pores on a surface of the plunger layer, wherein
the at least two sensors are arranged on, in or below a first surface, a second surface being formed by the surface of the plunger layer which lies opposite the sensor array,
the plunger is arrangeable in a first position such that the second surface is at a distance from the first surface, and wherein the plunger is arrangeable in a second position such that the second surface and the first surface are in direct contact, and
the pores of the porous plunger layer further include a diameter in the range of 0.05 to 200 micrometers, and
the open pores have a diameter which is greater than a diameter of the sensors.

2. The apparatus as claimed in claim 1, wherein at least one of
the space between the sensor array and the plunger layer is finable or is filled partly or completely with liquid; and
only pores at the surface of the porous plunger layer are finable or are filled with liquid, wherein pores inside the plunger layer at least one of do not contain any liquid and cannot be filled with liquid.

3. The apparatus as claimed in claim 1, wherein the at least two sensors are electrochemical sensors.

4. The apparatus as claimed in claim 1, wherein the at least two sensors are constructed from at least one of gold, silver, silver chloride, platinum, palladium and copper, or contain compounds or alloys of said metals.

5. The apparatus as claimed in claim 1, wherein
the layer thickness of the plunger layer is in the range of at least one of micrometers, millimeters, and centimeters; and
the plunger layer includes film opposite the sensor array.

6. The apparatus as claimed in claim 1, wherein the first surface is a first planar surface and wherein the second surface is a second planar surface.

7. The apparatus as claimed in claim 1, wherein the distance from the first surface is a distance in the range of micrometers or millimeters.

8. An apparatus comprising:
a sensor array including at least two sensors separated by walls; and
a plunger for detecting liquids or substances from liquids in reaction spaces that are spatially separated from one another when the plunger is in contact with the sensor array, the plunger being arranged to be movable relative to the sensor array and including a plunger layer, at a surface lying opposite the sensor array, capable of being brought into mechanical contact with the sensor array, the plunger layer further including at least partly or completely porous properties and being impermeable to liquids or substances from liquids relative to a total layer thickness of the plunger layer, wherein the pores are configured to receive the walls in open pores on a surface of the plunger layer, wherein
between the at least two sensors, the walls project from a first surface, which in each case completely surround or enclose the sensors particularly in the plane of the first surface and whose height with which the walls project from the first surface is greater than any height of structures which are arranged within parts of the first surface which are surrounded or enclosed by the walls, and wherein
a height and width of the walls between the at least two sensors is of the order of magnitude of the diameters of the pores of the plunger layer, and
in the second position of the plunger, the walls projecting from the first surface are arrangeable partly or completely in the pores of the plunger layer.

9. The apparatus as claimed in claim 8, wherein, as a result of a direct contact between the walls and the plunger layer, at least one of a gas- or liquid-tight connection exists and gas or liquid exchange is only possible via the pores which are arranged directly above the sensors.

10. The apparatus as claimed in claim 8, wherein at least one of
the porous plunger layer is formed from a porous material which contains porous plastic, porous rubber or porous natural rubber or is formed therefrom, and
the plunger layer is composed of a plastically deformable material, and the walls are constructed from an elastic material.

11. The apparatus as claimed in claim 8, wherein, as a result of a direct contact between the walls and the plunger layer, at least one of a gas- or liquid-tight connection exists and gas or liquid exchange is only possible via the pores which are arranged directly above the sensors.

12. The apparatus as claimed in claim 3, wherein the at least two sensors are metal electrodes arranged in finger-shaped fashion on the first surface.

13. A smart card or cassette comprising:
the apparatus as claimed in claim 1, wherein a chip comprises the sensor array.

14. A read-out device, wherein the smart card or cassette of claim 13 is inserted into the read-out device, the read-out device comprising:
a plunger actuator.

15. The read-out device as claimed in claim 14, wherein a pressure is exerted by the read-out device on the smart card or cassette, and the plunger layer pressed onto the chip is brought into mechanical contact with the chip surface in such a way that regions filled with liquid to be analyzed do not exchange liquid across different sensors, as a result of which closed-off reaction regions are formed above the respective sensors and/or pore volumes are decreased.

16. A method comprising:
using the read-out device as claimed in claim 14 in at least one of an immunological fast test, a blood test, a DNA or RNA analysis, an antibody test, a peptide test and an enzyme substrate test.

17. An apparatus comprising:
a sensor array including at least two sensors separated by walls; and
a plunger for detecting liquids or substances from liquids in reaction spaces that are spatially separated from one another when the plunger is in contact with the sensor array, the plunger being arranged to be movable relative to the sensor array and including a plunger layer, at a surface lying opposite the sensor array, capable of being brought into mechanical contact with the sensor array, the plunger layer further including at least partly or completely porous properties and being impermeable to liquids or substances from liquids relative to a total layer thickness of the plunger layer, wherein the pores are configured to receive the walls in open pores on a surface of the plunger layer, wherein the at least two sensors are arranged on, in or below a first surface, a second surface being formed by the surface of the plunger layer which lies opposite the sensor array, the plunger is arrangeable in a first position such that the second surface is at a distance from the first surface, and wherein the plunger is arrangeable in a second position such that the second surface and the first surface are in direct contact, and wherein pores of the porous plunger layer include a diameter in the range of 1 to 10 micrometers, and a diameter which is greater than the distance between electrodes of the sensors.

18. A method comprising:
using the read-out device as claimed in claim 15 in at least one of an immunological fast test, a blood test, a DNA or RNA analysis, an antibody test, a peptide test and an enzyme substrate test.

19. A method comprising:
using the smart card or cassette as claimed in claim 13 in at least one of an immunological fast test, a blood test, a DNA or RNA analysis, an antibody test, a peptide test and an enzyme substrate test.

* * * * *